United States Patent [19]
Tweden et al.

[11] Patent Number: 6,013,106
[45] Date of Patent: Jan. 11, 2000

[54] MEDICAL ARTICLE WITH ADHERED ANTIMICROBIAL METAL IONS AND RELATED METHODS

[75] Inventors: Katherine Tweden, Mahtomedi; Matthew F. Ogle, St. Paul, both of Minn.

[73] Assignee: St. Jude Medical, Inc., St. Paul, Minn.

[21] Appl. No.: 08/787,139

[22] Filed: Jan. 22, 1997

[51] Int. Cl.$^7$ ........................................................ A61F 2/54
[52] U.S. Cl. .................................... 623/66; 623/1; 623/11
[58] Field of Search ............................ 623/1, 2, 11, 901, 623/66; 427/2.24, 2.25, 2.28, 2.3

[56] References Cited

U.S. PATENT DOCUMENTS

| | | |
|---|---|---|
| 4,054,139 | 10/1977 | Crossley . |
| 4,411,648 | 10/1983 | Davis et al. . |
| 4,456,589 | 6/1984 | Holman et al. . |
| 4,476,590 | 10/1984 | Scales et al. . |
| 4,479,795 | 10/1984 | Mustacich et al. . |
| 4,483,688 | 11/1984 | Akiyama . |
| 4,563,485 | 1/1986 | Fox, Jr. et al. . |
| 4,569,673 | 2/1986 | Tesi . |
| 4,581,028 | 4/1986 | Fox, Jr. et al. . |
| 4,592,920 | 6/1986 | Murtfeldt . |
| 4,603,152 | 7/1986 | Laurin et al. . |
| 4,612,337 | 9/1986 | Fox, Jr. et al. . |
| 4,615,705 | 10/1986 | Scales et al. . |
| 4,846,844 | 7/1989 | De Leon et al. . |
| 4,847,049 | 7/1989 | Yamamoto . |
| 4,902,503 | 2/1990 | Umemura et al. . |
| 4,923,450 | 5/1990 | Maeda et al. . |
| 4,933,178 | 6/1990 | Capelli . |
| 4,973,320 | 11/1990 | Brenner et al. . |
| 5,019,096 | 5/1991 | Fox, Jr. et al. . |
| 5,049,139 | 9/1991 | Gilchrist . |
| 5,049,140 | 9/1991 | Brenner et al. . |
| 5,059,186 | 10/1991 | Yamamoto et al. . |
| 5,207,706 | 5/1993 | Menaker . |
| 5,443,813 | 8/1995 | Hainfeld . |
| 5,454,886 | 10/1995 | Burrell et al. . |
| 5,468,562 | 11/1995 | Farivar et al. . |
| 5,474,797 | 12/1995 | Sioshasi et al. . |
| 5,516,480 | 5/1996 | Krall et al. . |
| 5,520,664 | 5/1996 | Bricault, Jr. et al. . |
| 5,630,804 | 5/1997 | Imada et al. . |
| 5,662,913 | 9/1997 | Capelli . |

FOREIGN PATENT DOCUMENTS

| | | |
|---|---|---|
| 0 190 504 A2 | 12/1985 | European Pat. Off. . |
| 0 206 024 A2 | 6/1986 | European Pat. Off. . |
| 0 516 184 A1 | 11/1988 | European Pat. Off. . |
| 0 328 421 A2 | 2/1989 | European Pat. Off. . |
| 0 596 615 A1 | 10/1993 | European Pat. Off. . |
| WO 93/07924 | 4/1993 | WIPO . |
| WO 93/23092 | 11/1993 | WIPO . |
| WO 96/01119 | 1/1996 | WIPO . |
| WO 97/27886 | 7/1997 | WIPO . |

OTHER PUBLICATIONS

Babycos et al., "A Prospective Randomized Trial Comparing the Silver–Impregnated Collagen Cuff With the Bedside Tunneled Subclavian Catheter", J. of Parenteral and Enteral Nutr., vol. 17, No. 1, pp. 61–63 (1993).

Bambauer et al., "Frequency, Therapy, and Prevention of Infections Associated With Large Bore Catheters", ASAIO Journal, vol. 38, No. 2, pp. 96–101 (1992).

Bambour et al., "New Surface–Treatment Technologies for Catheters Used for Extracorporeal Detoxification Methods", Dialysis & Transplantation, vol. 24, No. 5, pp. 288–237 (1995).

Butcher et al., "The Treatment of Large Cutaneous Burns With Silver Creams", The Journal of Trauma, vol. 9, No. 5, pp. 359–376 (1969).

Chervu et al., "Efficacy and Duration of Antistaphylococcal Activity Comparing Three Antibiotics Bonded to Dacron Vascular Grafts With a Collagen Release System", J. of Vascular Surgery, 13:897–901 (1991).

Clark et al., "Antibacterial Vascular Grafts With Improved Thromboresistance", Arch. Surg., vol. 109, pp. 159–162 (1974).

Deitch et al., "Results of a Multicenter Outpatient Burn Study on the Safety and Efficacy of Dimac–SSD, a New Delivery System for Silver Sulfadiazine", J. of Trauma, vol. 29, No. 4, pp. 430–434 (1989).

Didisheim et al., "Infectious and Thromboembolism With Implantable Cardiovascular Devices", Trans. Am. Soc. Artif. Intern. Organs, vol. XXXV, pp. 54–70 (1989).

Dunkirk et al., "Photochemical Coatings for the Prevention of Bacterial Colonization", J. of Biomaterials Applications, vol. 6, No. 2, pp. 131–156 (1991).

French et al., "Rifampicin Antibiotic Impregnation of the St. Jude Medical Mechanical Valve Sewing Ring: A Weapon Against Endocarditis", J. of Thoracic and Cardiovascular Surgery, vol. 112, No. 2, pp. 248–252 (1996).

Gravens et al., "The Antibacterial Effect of Treating Sutures With Silver", Surgery, vol. 73, No. 1, pp. 122–127 (1973).

Haynes et al., "Anitbacterial Silver Surfaces–An Assessment of Needs and Opportunities for Clinical Devices", Abstract, Proceedings on the First Intl. Conference on Gold and Silver in Medicine, Bethesda, MD, May 1987.

(List continued on next page.)

*Primary Examiner*—Michael J. Milano
*Attorney, Agent, or Firm*—Westman, Champlin & Kelly, P.A.; Peter S. Dardi; Hallie A. Finucane

[57] ABSTRACT

Biocompatible articles for placement in a patient are described having releasably adhered antimicrobial metal ions. Furthermore, biocompatible articles made from biocompatible material for subcutaneous, percutaneous and cutaneous use are described where the biocompatible material has an attached exogenous storage structure with reversibly bound antimicrobial metal ions. The exogenous storage structures can include proteins such as ferritin, globulins, albumin, glutathione, transferrin, hemoglobin, metallothiens, myoglobin, ceruloplasmin and hemocyanin. Associated methods for imparting antimicrobial properties to biocompatible articles are described.

8 Claims, No Drawings

OTHER PUBLICATIONS

Jansen et al., "In Vitro Evaluation of the Antimicrobial Efficacy and Biocompatibility of a Silver–Coated Central Venous Catheter", J. of Biomaterials Applications, vol. 9, pp. 55–70 (1994).

Kinney et al., "Antibiotic–Bonded PTFE Vascular Grafts: The Effect of Silver Antibiotic on Bioactivity Following Implantation", J. of Surgical Research, 50:430–435 (1991).

Liedberg, Hans, "Catheter Induced Urethral Inflammatory Reaction and Urinary Tract Infection", Scandinavian Journal of Urology and Nephrology, Suppl. No. 124 (Stockholm 1991), pp. 2–43.

Mermel et al., "Surface Antimicrobial Activity of Heparin–Bonded and Antiseptic–Impregnated Vascular Catheters", J. of Infectious Diseases, 167:920–924 (1993).

Olanoff et al., "Sustained Release of Gentamicin From Prosthetic Heart Valves", Trans. Am. Soc. Artif. Intern. Organs. vol. XXV, pp. 334–338 (1979).

Oloffs et al., "Biocompatibility of Silver–Coated Polyurethane Catheters and Silver–Coated Dacron™ Materials", Biomaterial, vol. 15, No. 10, pp. 753–758 (1994).

Riley et al., "A Large Randomized Clinical Trial of a Silver–Impregnated Urinary Catheter: Lack of Efficacy and Staphylococcal Superinfection", The American Journal of Medicine, vol. 98, pp. 349–356 (1995).

Sioshansi, Piran, "New Processes for Surface Treatment of Catheters", Artificial Organs, 18(4):266–271 (1994).

Tobin et al., "Reduced Bacterial Colonization of External Fixation Pins", Surfaces in Biomaterials Foundation, pp. 19–22 (1995).

MEDICAL ARTICLE WITH ADHERED ANTIMICROBIAL METAL IONS AND RELATED METHODS

FIELD OF THE INVENTION

The invention relates to biocompatible articles having antimicrobial metal ions releasably bound to the article. Release of the metal ions following contact of the article with a patient's bodily fluids reduces the risk of infection.

BACKGROUND OF THE INVENTION

A variety of medical articles are designed particularly for contact with a patient's bodily fluids. The duration of this contact may be relatively short, as is typical with wound dressings, or may be long term, as is typical with prosthetic heart valves implanted into the body of a recipient. Some articles such as catheters can have either short term or relatively long term contact. Other articles typically having relatively short term contact with the patient include, without limitation, burn dressings and contact lenses. Other articles typically having long term contact with a patient include, without limitation, prostheses.

Prostheses, i.e., prosthetic articles, are used to repair or replace damaged or diseased organs, tissues and other structures in humans and animals. Prostheses generally must be biocompatible since they are typically implanted for extended periods of time. Examples of prostheses include, without limitation, artificial hearts, artificial heart valves, ligament repair materials, vessel repair and replacement materials, and surgical patches. Prostheses can be constructed from natural material, synthetic material or a combination of natural and synthetic materials.

The ability to replace or repair diseased heart valves with prosthetic devices has provided surgeons with a method of treating heart valve deficiencies due to disease and congenital defects. A typical procedure involves removal of the natural valve and surgical replacement with a mechanical or bioprosthetic valve. Another technique uses an annuloplasty ring to provide structural support to the natural root, which supports the natural annulus of the valve.

Contact of any exogenous articles with bodily fluids creates a risk of infection. This risk can be very serious and even life threatening. In addition, considerable costs, and longer or additional hospital stays may result due to infection. For example, infections associated with dressings can increase the seriousness of the injury for burn victims. Also, infection associated with an implanted prosthesis can necessitate replacement of the device.

Infections are a particularly common complication resulting from the use in hospitals of percutaneous devices such as catheters. Infections related to catheter use can result from intracutaneous invasion during catheter insertion or from invasion by way of the exit site during use. Adherence of bacteria to the catheter surface complicates treatment of the infection.

Physicians use a variety of prostheses to correct problems associated with the cardiovascular system, especially the heart. Prosthetic Valve Endocarditis (PVE) is an infection that can be associated with a heart valve prosthesis. Bacteria can form colonies at the wound associated with the implant and in the fabric of the sewing cuff of the valve prosthesis. The growth of tissue into the sewing cuff material also is associated with the attachment of bacteria and other pathogens. For this reason, heart valve recipients are cautioned regarding activities that may introduce bacteria into the bloodstream, such as dental work. For tissue replacement valves, PVE more commonly is associated with the leaflet portion of the valve rather than the sewing cuff portion of the valve.

PVE can be caused by gram-negative bacteria, gram-positive bacteria, fungus or rickettsia. PVE caused by gram-positive bacteria is particularly prevalent. Diagnosis is based generally on two positive blood cultures for the same organism along with compatible clinical symptoms. Certain organisms are difficult to culture, however, which can complicate diagnosis.

With respect to replacement heart valves, care must be taken to ensure sterility during production and to prevent contamination during the replacement valve implantation process. For example, to ensure sterility or to reduce perioperative contamination, some surgeons apply antibiotics to the prosthesis prior to implantation. These techniques, however, have relatively short-term effectiveness. In spite of these efforts, PVE occurs in about 2 percent to 4 percent of patients.

Infections occurring within the first 60 days after valve replacement are termed early onset PVE while infections occurring more than 60 days after valve implantation are termed late onset PVE. Mortality rates for early onset PVE range from 56 percent to 88 percent. Mortality rates for late onset PVE range from 30 percent to 53 percent. These high mortality rates emphasize the seriousness of these infections. Similar infections are associated with other prostheses.

SUMMARY OF THE INVENTION

The invention offers a versatile approach to reducing the risk of infection associated with contact of exogenous articles with bodily fluids of a patient. The use of antimicrobial metal cations provides for long term antimicrobial activity in contrast with more transient antimicrobial agents. This long term antimicrobial activity provides a reduction in the risk of infection. At the same time, conditions used to treat the biocompatible material are relatively mild, so these approaches can find wide spread applicability.

In a first aspect, the invention involves a biocompatible article encompassing a prosthesis suitable for implantation, the prosthesis including tissue and/or biological polymer with antimicrobial metal ions releasably adhered thereto. In a preferred embodiment of the biocompatible article, at least a portion of the adhered antimicrobial metal ions is provided by an exogenous storage structure having metal ions releasably bound thereto, the exogenous storage structure being attached to the biocompatible material. The exogenous storage structure may comprise a protein, such as ferritin. In another embodiment, the exogenous storage structure may comprise a chelating agent.

In the biocompatible article, the tissue preferably is selected from the group consisting of crosslinked tissues and uncrosslinked tissues. In one embodiment, the tissue may comprise crosslinked, collagen-containing tissue, where at least a portion of the adhered antimicrobial metal ions is provided by directly adhered silver ions. In preferred embodiments, the antimicrobial metal ions comprise Ag ions.

In another aspect, the invention involves a biocompatible article including a biocompatible material, an exogenous storage structure attached to the biocompatible material and antimicrobial metal ions reversibly bound to the exogenous storage structure. Preferred exogenous storage structures include, without limitation, proteins such as ferritin, globulins, albumin, glutathione, transferrin, hemoglobin, metallothiens, myoglobin, ceruloplasmin and hemocyanin. The exogenous storage structures may be attached to the biocompatible material by covalent bonds or by specific binding interactions.

In another aspect, the invention involves a method of preparing a biocompatible article including the step of adhering antimicrobial metal ions to a tissue and/or biological polymer to form a prosthesis suitable for implantation, such that the antimicrobial metal ions are released following implantation of the biocompatible article into a patient. The method can include adhering the antimicrobial metal ions to the biocompatible material by attaching an exogenous storage structure to the biocompatible material, where the exogenous storage structure has antimicrobial metal ions reversibly bound thereto.

The method of preparing a biocompatible article further can include the step of selecting the exogenous storage structure to be capable of reversibly storing antimicrobial metal ions such that the metal ions are effective at reducing incidence of infection without resulting in plasma levels of metal ions sufficiently high to induce observable symptoms following attachment of the exogenous storage structure to the biocompatible material and release of said metal ions. In the method of preparing a biocompatible article, the biocompatible article can be a prosthetic article suitable for implantation in the patient or a percutaneous device. In the method, preferred antimicrobial metal ions include Ag ions.

In another aspect, the invention involves a method of preparing a biocompatible article comprising the steps of releasably binding antimicrobial metal ions to an exogenous storage structure and attaching the exogenous storage structure to a biocompatible material.

DESCRIPTION OF THE PREFERRED EMBODIMENTS

The present invention involves use of antimicrobial metal ions from metal salts to inhibit development of an infection that can be associated with contact of various medical articles with bodily fluids. These bodily fluids include, without limitation, blood, plasma, serum, interstitial fluids, saliva and urine. Appropriate metal ions include cations of Ag, Au, Pt, Pd, Ir, Cu, Sn, Sb, Bi, Zn and combinations thereof. A preferred cation is Ag.

Biocompatible articles are suitable for contact with bodily fluids of a patient. The patient can be an animal, especially a mammal, and preferably is a human. Relevant biocompatible articles generally incorporate a biocompatible material with adhered antimicrobial metal ions. Antimicrobial metal ions can be adhered directly to the biocompatible material, as described below. Alternatively, the antimicrobial metal ions can be adhered indirectly to the biocompatible material, where the antimicrobial metal ions are bound to an exogenous storage structure that is attached to the biocompatible material. The exogenous storage structures reversibly bind antimicrobial metal ions for gradual release of the metal ions.

Coatings of silver metal have been used to impart antimicrobial properties to certain medical devices. The antimicrobial effect of silver metal is thought to result from release of silver ions that slowly form from the silver metal. The substrate receiving the silver coating, however, must be able to withstand the harsh, vacuum conditions generally used in the deposition of the silver metal. Extremely small quantities of silver ions that potentially may be associated at a particular time with silver metal-coated articles do not constitute silver ions adhered to an article as described herein. Silver ions have been adhered in certain forms to burn dressings, sutures and polyester grafts to investigate antimicrobial properties.

Adhered silver ions, or other metal ions, in the present invention are stored in the form of a salt rather than in the form of a metal. Approaches based on antimicrobial metal salts and corresponding metal cations permit employment of different and generally less harsh conditions in comparison with conditions used for the application of silver metal. Also, the use of antimicrobial metal salts creates the potential for greater control of the release rate of ions. This is important since at least silver is toxic to mammals in sufficiently high quantities. Therefore, it is advantageous to select the level of silver ions or other metal ions to reduce the risk of infection while minimizing exposure of the patient to the metal cations.

Healthy humans generally have plasma levels of Ag of about 0.2 $\mu$g/l to about 10 $\mu$g/l, where 10 $\mu$g/l corresponds to about 0.01 ppm or 10 ppb. In the blood, silver ions are carried by high molecular weight proteins, such as glutathione and transferrin. Silver cations are removed from the body with about 90 percent being excreted in bile and significant amounts being excreted in urine.

Serum silver ion concentrations of about 300 ppb have been associated with toxic symptoms including argyria in gingiva and cheeks, nephrotic syndrome and leukopenia. Silver ion concentrations of about 40 $\mu$mol/l (about 4 mg/l) are known to cause rapid cell death. Therefore, it is preferable to keep silver ion concentrations in the blood stream safely below these toxic levels and preferably below levels where any symptoms are observable.

A biocompatible article includes a biocompatible material that acts as a substrate for the formation of the article. The biocompatible material has adhered antimicrobial metal ions. The antimicrobial metal ions can be directly adhered to the biocompatible material. More preferably, the silver ions are adhered to an exogenous storage structure that is, in turn, attached to or contained within the structure of the biocompatible material.

The use of exogenous storage structures can provide flexibility in directing the antimicrobial cations to specific, particularly infection susceptible portions of the article. Furthermore, use of an exogenous storage structure permits control of the release rate of the metal ions. The association of antimicrobial metal ions with the exogenous storage structures can be performed before or after attachment of the exogenous storage structures to the biocompatible material.

A. Biocompatible Articles

Relevant biocompatible articles include all medical articles that contact bodily fluids. These articles can be organized roughly into three groups: implanted devices, percutaneous devices and cutaneous devices. Implanted devices broadly include articles that are fully implanted in a patient. Percutaneous devices include items that penetrate the skin, thereby extending from outside the body into the body. Cutaneous devices are used superficially, for example, at a wound site or at a moist membrane.

Implanted devices include, without limitation, prostheses such as transplant organs, heart valve prostheses, pericardial patches, vascular grafts, biological conduits, annuloplasty rings, bone, skin, ligaments and tendons. Percutaneous devices include without limitation catheters of various types. Catheters can be used for accessing various bodily systems such as the vascular system, the gastrointestinal tract, or the urinary system. Cutaneous devices include, without limitation, skin grafts, burn dressings, wound dressings of all types, and contact lenses. These biocompatible articles can be made from the biocompatible materials described below.

B. Biocompatible Materials

Appropriate biocompatible materials include natural materials, synthetic materials and combinations thereof. Natural, i.e., biological, material for use in the invention includes relatively intact tissue as well as decellularized tissue. These tissues may be obtained from, for example, natural heart valves; portions of natural heart valves such as roots, walls and leaflets; pericardial tissues such as pericardial patches; connective tissues; bypass grafts; tendons; ligaments; skin patches; blood vessels; cartilage; dura matter; skin; bone; umbilical tissues; and the like.

Natural tissues are derived from a particular animal species, typically mammalian, such as human, bovine, porcine, seal or kangaroo. These natural tissues generally include collagen-containing material. Natural tissue is typically, but not necessarily, soft tissue. Appropriate tissues also include tissue equivalents such as a tissue-engineered material involving a cell-repopulated matrix, which can be formed from a polymer or from a decellularized natural tissue.

Biological tissues can be fixed by crosslinking. This provides mechanical stabilization, for example, by preventing enzymatic degradation of the tissue. Glutaraldehyde is typically used for fixation, but other fixatives can be used, such as epoxides and other difunctional aldehydes. Biological materials can be used in either crosslinked or uncrosslinked form, depending on the type of tissue, the use and other factors.

Relevant synthetic materials can be polymers. Polymeric materials can be fabricated from synthetic polymers as well as purified biological polymers. Appropriate synthetic materials include hydrogels and other synthetic materials that cannot withstand severe dehydration.

Appropriate synthetic polymers include without limitation polyamines (e.g., nylon), polyesters, polystyrenes, polyacrylates, vinyl polymers (e.g., polyethylene, polytetrafluoroethylene, polypropylene and poly vinyl chloride), polycarbonates, polyurethanes, poly dimethyl siloxanes, cellulose acetates, polymethyl methacrylates, ethylene vinyl acetates, polysulfones, nitrocelluloses and similar copolymers. These synthetic polymeric materials can be woven into a mesh to form a matrix or substrate. Alternatively, the synthetic polymer materials can be molded or cast into appropriate forms.

Biological polymers can be naturally occurring or produced in vitro by, for example, fermentation and the like. Purified biological polymers can be appropriately formed into a substrate by techniques such as weaving, knitting, casting, molding, extrusion, cellular alignment and magnetic alignment. For a description of magnetic alignments see, for example, R. T. Tranquillo et al., Biomaterials 17:349–357 (1996). Suitable biological polymers include, without limitation, collagen, elastin, silk, keratin, gelatin, polyamino acids, cat gut sutures, polysaccharides (e.g., cellulose and starch) and copolymers thereof.

Biocompatible materials can include a combination of the various natural materials and synthetic polymer materials described above. The biocompatible materials also can include metal or ceramic portions, and some relevant prostheses are made completely from metal, ceramics or combinations of metal and ceramics. Mechanical heart valves are relevant products, which generally are made out of metal and/or ceramic components. Appropriate ceramics include, without limitation, hydroxyapatite, alumina and pyrolytic carbon.

There are certain situations where multiple biological activities are desirable. In these situations, materials can be made by forming a bioactive coating on a base material, where the bioactive coating can include, for example, cell adhesion molecules, anticoagulants such as heparin and hiurdin, or growth factors such as the fibroblast growth factors, platelet-derived growth factors, transforming growth factors, epidermal growth factors, insulin-like growth factors I and II, platelet-derived endothelial cell growth factors, vascular endothelial growth factor, and combinations thereof. Articles with bioactive coatings then can be subjected to further application of antimicrobial metal ions using the techniques described herein. In some cases, the order of the application of the metal ions and the other bioactive material can be reversed, or the application of the metal ions and other bioactive material can be performed simultaneously.

C. Direct Adhering of Antimicrobial Metal Ions

For some applications it may be adequate to directly adhere the antimicrobial metal ions to a biocompatible material by contacting the biocompatible material with a solvated metal salt. For example, treating biological materials with significant concentrations of Ag cations in solution results in Ag cations adhering to the material. For certain materials, sufficient quantities of antimicrobial metal ions will be complexed to the material to result in slow release of cations upon use of the article, thereby inhibiting infection for extended periods.

With natural materials, silver ions may become associated with sulfur and selenium generally and with a variety of proteins such as endogenous metal ion storage proteins and metallothioneines, which have large amounts of sulfhydryl groups. The ions may also become associated with other chemical functional groups within the material.

Biocompatible materials are contacted with an antimicrobial metal salt solution, where the time of contact and the concentration preferably are adjusted to yield the desired level of bound metal ions. For silver cations, appropriate silver salts include silver nitrate and silver sulphadiazine. Chelating agents also can be added to enhance the direct adhering of the metal cations to the biocompatible material.

It is possible that association of antimicrobial metal cations with natural biological substrates may involve binding with naturally occurring (i.e., endogenous) ferritin. Ferritin is an iron storage protein that can store relatively large quantities of iron ions, for example, several thousands of iron ions per protein molecule. Ferritin can also store similar quantities of other non-ferrous metal ions. Naturally occurring ferritin may be crosslinked or otherwise bound to a protein or other biological or synthetic substrate during fixation. Under these conditions, the natural ferritin can slowly release associated cations into the local environment.

D. Exogenous Storage Structures

Storage structures can be used for the storage and controlled release of antimicrobial metal cations into the surrounding fluid. Exogenous storage structures preferably are microscopic, macromolecular compositions such as natural or synthetic proteins or appropriate synthetic polymers. It is to be understood, however, that aggregations of the preferred compositions need not be microscopic. The term "protein" includes peptides and polypeptides alone as well as peptides and polypeptides conjugated with carbohydrates, nucleic acids and or lipids. Exogenous storage structures are distinct from any naturally occurring structures, such as ferritin already present in the material.

Appropriate protein storage structures within the scope of the present invention include metal binding proteins such as ferritin, transferrin, hemoglobin, globulins, albumin, glutathione, metallothiens, myoglobin, ceruloplasmin and hemocyanin, as well as modified proteins having attached bifunctional chelators to generate metal binding capability. Ferritin is a preferred metal binding protein because of its generally large storage capacity.

Ferritin protein without bound metal is called apoferritin. Apoferritin is a 24-subunit protein with a molecular weight of approximately 450,000, although the molecular weight varies depending on the animal species from which the ferritin is isolated. Isoferritins, related proteins with differing numbers of subunits, are also within the scope of the present invention and are included within the term "ferritin."

The ferritin core can store between about 2000 and about 4500 iron ions. For example, horse spleen ferritin can bind about 4500 iron ions, while human ferritin can bind about 2500 iron ions. The iron is stored within the core as ferric oxide or ferric hydroxyphosphate. Ferritin can also bind large quantities of other metal ions including ions of the following metals: Al, Mg, Be, Cu, Zn, V, Tb, Cd, Ag. Binding of these non-iron ions is enhanced by the simultaneous binding of a moderate quantity of iron ions. The binding of iron or non-iron metal ions occurs both in vitro and in vivo. Generally, storage structures such as ferritin can be bound to tissue with the storage structures preloaded in vitro with silver ions or other metal ions.

The selection of a particular storage structure can be based on its storage capacity and the release rate of the stored metal salt. For example, ferritin or other metal binding proteins generally need not be saturated with the metal ion or ions of interest to be useful in the invention. The ferritin can be charged with, for example, Ag by incubating purified ferritin with a relatively concentrated AgCl solution or other convenient silver salt solution. The binding of the ions to the protein can be accelerated by heating and by pH adjustment. After a sufficient period of incubation, the free metal ions can be removed by passing the solution over an ion exchange resin or through a size exclusion membrane.

In addition, storage structures can be formed from other proteins modified to create metal binding capability. Preferred proteins for modification have high molecular weight, such as immunoglobulins. The modification can involve, for example, covalent bonding of metal sequestering compounds to the protein.

More specifically, significant metal binding capability can be created by binding a bifunctional chelator, such as a polyaminocarboxylate or a polyaminophosphonate, to the protein as the metal sequestering compound. Preferred bifunctional chelators include electrophilic and nucleophilic moieties such as bromoacetamide, maleimide, imidoester, thiophthalimide, N-hydroxysuccinimyl ester, pyridyl disulfide, phenyl azide, o-acylisourea, diazonium hydrazine, carbonyl hydrazine, amino hydrazine, acyl hydrazine, diazonium semicarbazide, carbonyl semicarbazide, amino semicarbazide, acyl semicarbazide, thio semicarbazides and cyclic polyaminocarboxylates and cyclic polyaminophosphonates having 12 to 16 atom rings. The specific chelator can be selected to produce a desired release rate of the bound metal ions.

The bifunctional chelators generally can be covalently bonded to the protein by conventional methods. Typically, the covalent bonds will be formed between selected amino acid residues of the protein and a specific functional group in the chelator. The number of chelating agents bound to a protein will depend on the structures and the reaction conditions.

It is preferable to have at least one bifunctional chelator bound to each protein, and it is more preferable to have multiple bifunctional chelators bound to each protein. Metal ions can be bound to the chelator before, at the time of, or after the covalent binding of the chelator to the protein. The reaction conditions may influence the selected order of the processing steps.

As an alternative to use of a metal storage protein for storing metal cations, the exogenous metal storage structure can be formed from a synthetic organometallic polymer. For example, polymers involving norbornadiene-silver nitrate complexes can be used. Generally, the particular organometallic polymers can be selected based on the desired binding capacity and release rate.

E. Binding of the Exogenous Storage Structures

Binding of the exogenous storage structures to the biocompatible material can involve specific binding interactions to target specific structures within the material. Alternatively, the binding can involve nonspecific binding due, for example, to reaction with general crosslinking agents. The use of general crosslinking agents generally precludes exogenous storage structures from being concentrated at particular locations within the biocompatible material. The binding of the exogenous storage structures preferably takes place at or near a physiological pH, preferably ranging from a pH of about 6 to a pH of about 8.5 and more preferably from a pH of about 7.0 to a pH of about 8.0.

A typical procedure for non-specific binding makes use of glutaraldehyde, which crosslinks proteins by way of two aldehyde groups. Since glutaraldehyde is typically used for fixation of some biocompatible materials, the non-specific crosslinking to bind the exogenous storage structures to the biocompatible material can be performed simultaneously with fixation of the tissue. Alternatively, the non-specific crosslinking to bind the exogenous storage structures can be performed as a separate step before or after the completion of a fixation process, assuming a fixation step is performed.

The targeting of particular locations can be useful since it has been observed that infection tends to initiate more frequently in certain locations. Examples of suitable targets include heart valve leaflets. The character of the targeted binding can be covalent or can involve a plurality of non-covalent interactions such as hydrogen bonding, van der Waals interactions and molecular rearrangements, which characterize, for example, antibody-antigen, specific binding protein-receptor and enzyme-substrate associations.

A preferred method of targeting a particular location involves covalent binding of a linker to the storage structure and association of the linker with the prosthetic material by a plurality of non-covalent interactions. A variety of commercially available antibodies and other specific binding reagents may be used as linkers. Such linkers can function as targeting molecules to target cellular or extracellular sites having specific binding sites.

Alternatively, cellular or extracellular components at a preferred location of a biological material can be isolated by conventional techniques. For example, nuclear membranes or a specific portion of the nuclear membrane corresponding to an antigen or groupings of antigens can be isolated. The isolated materials then are used to produce polyclonal or monoclonal antibodies by conventional techniques. The resulting antibodies are covalently bonded to the exogenous storage structure to prepare it for binding to the biocompatible material.

A storage structure having an attached antibody or any other comparable targeting molecule is considered a "storage structure" for the purposes of the present application. The binding of compounds to antibodies is well established, especially where the compound is a protein. Due to its high iron content, ferritin is commonly linked to antibodies to serve as an electron microscopy probe in the histology field. In a preferred embodiment, glutaraldehyde is used to connect the respective proteins. In addition, as noted above, the antibody itself can be modified with sequestering agents to become, itself, an exogenous storage structure, rather than serving as a linker portion of an exogenous storage structure.

In an alternative embodiment, photochemical coupling can be used for specific or nonspecific covalent coupling. Photochemical coupling is based on the use of high energy light, e.g., ultraviolet light, to form reactive intermediates of certain functional groups. These reactive intermediates can form carbon-carbon bonds between two compositions. Aryl ketone functional groups are particularly useful in this respect.

Photochemical coupling is particularly appropriate for the attachment of exogenous storage structures to synthetic polymeric materials, uncrosslinked tissues or biological polymers. See, for example, Dunkirk et al., J. Biomaterials Applications 6:131–156 (1991). Photochemical techniques are useful also for the attachment of exogenous storage structures to metal surfaces and decellularized tissue substrates. Photochemical coupling can be used for the direct attachment of an exogenous storage structure to the biocompatible material. Alternatively, photochemical coupling can be used to attach a linker to the biocompatible material either before or after the attachment of the linker to the exogenous storage structure.

F. Combination of Approaches

Direct adhering of antimicrobial metal cations can be combined with the indirect approach using exogenous storage structures. Contact of a biocompatible material with a metal salt solution to achieve direct adhering of antimicrobial metal cations can be done before or after attachment of exogenous storage structures. Selection of the exogenous storage structure may be adjusted in view of the combined treatment with metal salt solutions. For example, if the release rate of the directly adhered metal cations is not optimal, the release rate of the exogenous storage structures may be selected in the combined treatment approach to yield an effective reduction in risk of infection.

Furthermore, either direct or indirect adherence of antimicrobial metal cations to a biocompatible material can be combined with a silver metal coating process. Preferably, only a portion of the article is coated with silver metal. For example, the silver metal coating can be applied to one or more component parts of the article prior to assembly. Treatment with antimicrobial metal salts can be performed before or after performing the silver metal coating, or these steps can be performed independently with respect to different parts that are to be assembled into the final article. Alternatively, direct or indirect adherence of the metal cations can be performed as a final step after applying a silver metal coating and after assembly.

G. Combination with Anticalcification Agent

Polyvalent metal cations, especially $Al^{+3}$, have been shown to be useful in reducing calcification that is associated with implanted prostheses. Exogenous storage structures similar to those described above have been shown to be useful in delivering these polyvalent cations. See, copending U.S. patent application Ser. No. 08/690,661, incorporated herein by reference.

The anticalcification and antimicrobial approaches can be combined either by adhering two exogenous storage structures or by using a single exogenous storage structure or structures storing both types of agents. In a preferred embodiment, ferritin is used to store both $Al^{+3}$ and $Ag^{+1}$ cations. The relative amounts of the two types of cations can be optimized to produce the desired balance of beneficial effects.

EXAMPLES

The examples demonstrate the binding of silver cations to ferritin. Similar determinations were made for the simultaneous binding of silver ions and aluminum ions to ferritin.

Example 1

Silver Ions

Horse spleen ferritin (HS ferritin) was obtained from Sigma Chemical Company (Saint Louis, Mo.). A 0.25 ml quantity of a 100 mg/ml solution of HS ferritin was added to a test tube along with 1 ml of 0.1 M silver nitrate (ACS reagent grade from Aldrich Chemical Co. lot 17327BQ) solution. The test tube was covered with foil to prevent oxidative degradation of the silver nitrate solution. The covered tube was placed in an incubator at 47.0° C. for 36 hours shaking at 200 RPMs.

Following the 36 hours of shaking, the ferritin was dialyzed using a 500 Dalton pore dialysis membrane (Spectra Pour) against a 0.5 molar HEPES buffer saline solution at pH 7.2. Dialysis was continued until silver ion levels in the dialysate were considered baseline using an ICP-AES (Inductively Coupled Plasma-Atomic Emission Spectroscopy) instrument, an Atom Scan 16™ by Thermo Jarrell Ash Corp., Franklin, Mass. Then, the samples were hydrolyzed for elemental analysis. Approximately 28.4 silver ions along with 210 iron ions were bound per ferritin molecule. The iron ions presumably were associated with the ferritin as purchased. Iron can be easily removed with chelation before loading with silver, if desired.

Example 2

Silver Ions and Aluminum Ions

Horse spleen ferritin (HS ferritin) was obtained from Sigma Chemical Company (Saint Louis, Mo.). A 0.25 ml quantity of a 100 mg/ml solution of HS ferritin was added to a test tube along with 1 ml of 0.1 M silver nitrate (ACS reagent grade from Aldrich Chemical Co. lot 17327BQ) solution. The test tube was covered with foil to prevent oxidative degradation of the silver nitrate solution. The covered tube was placed in an incubator at 47.0° C. for 4 hours shaking at 200 RPMs. Then, 1 ml of 0.1 M aluminum chloride hexahydrate solution was added to the solution. The test tube was returned to the incubator for 32 hours of additional shaking at 47° C.

Following the 36 hours of shaking, the ferritin was dialyzed using a 500 Dalton pore dialysis membrane (Spectra Pour) against a 0.5 molar HEPES buffer saline solution at pH 7.2. Dialysis was continued until silver ion levels were considered baseline using an ICP-AES (Inductively Coupled Plasma-Atomic Emission Spectroscopy) instrument, an Atom Scan 16™ by Thermo Jarrell Ash Corp., Franklin, Mass. Then, the samples were hydrolyzed for elemental analysis. Approximately 28.4 $Ag^{+1}$ ions, 300 $Al^{+3}$ ions and 210 iron ions were bound per ferritin molecule. Again, the iron can be removed if desired.

What is claimed is:

1. A biocompatible article comprising a biocompatible material forming at least a portion of said biocompatible article, a macromolecular, exogenous storage structure bound to said biological material and antimicrobial metal ions reversibly bound to said exogenous storage structure.

2. The biocompatible article of claim 1, wherein said biocompatible material is selected from the group consisting of crosslinked tissues, uncrosslinked tissues and synthetic materials.

3. The biocompatible article of claim 1, wherein said exogenous storage structure comprises a protein.

4. The biocompatible article of claim 2, wherein said protein is ferritin.

5. The biocompatible article of claim 3, wherein said protein is selected from the group consisting of globulins, albumin, glutathione, transferrin, hemoglobin, metallothiens, myoglobin, ceruloplasmin and hemocyanin.

6. The biocompatible article of claim 1, wherein said antimicrobial metal ions comprise silver ions.

7. The biocompatible article of claim 1, wherein said attachment of said exogenous storage structure to said biocompatible material involves covalent bonding.

8. The biocompatible article of claim 1, wherein said attachment of said exogenous storage structure to said biocompatible material involves specific binding interactions.

* * * * *

UNITED STATES PATENT AND TRADEMARK OFFICE
CERTIFICATE OF CORRECTION

PATENT NO. : 6,013,106
DATED : January 11, 2000
INVENTOR(S) : Katherine Tweden and Matthew F. Ogle It is certified that error appears in the above-identified patent and that said Letters Patent is hereby corrected as shown below:

Title page,
Under [56] References Cited; Other Publications: 3rd reference
    Change "Bambour" to --Bambauer--.

Column 11, line 7, after "claim", change "2" to --3--.

Signed and Sealed this

Sixteenth Day of January, 2001

Attest:

Q. TODD DICKINSON

Attesting Officer

Commissioner of Patents and Trademarks